United States Patent [19]
Murphy et al.

[11] Patent Number: 5,492,541
[45] Date of Patent: Feb. 20, 1996

[54] DYE COMPOSITIONS CONTAINING 5,6-DIHYDROXY INDOLES AND A FOAM GENERATOR

[75] Inventors: Bryan P. Murphy, Monroe; Keith C. Brown, New Canaan, both of Conn.; Thomas M. Schultz, Highland Mills, N.Y.; Alice A. Meyer, Danbury, Conn.

[73] Assignee: Clairol Incorporated, Stamford, Conn.

[21] Appl. No.: 463,880

[22] Filed: Jan. 5, 1990

Related U.S. Application Data

[63] Continuation of Ser. No. 138,992, Dec. 29, 1987, abandoned, which is a continuation-in-part of Ser. No. 761,950, Aug. 2, 1985, abandoned.

[51] Int. Cl.$^6$ .................................................. A61K 7/13
[52] U.S. Cl. .................. 8/423; 8/406; 8/409; 424/47
[58] Field of Search ..................... 8/409, 423, 406; 424/47

[56] References Cited

U.S. PATENT DOCUMENTS

| | | | |
|---|---|---|---|
| 4,013,404 | 3/1977 | Parent et al. ............................. | 8/423 |
| 4,208,183 | 6/1980 | Grollier et al. ......................... | 8/409 |
| 4,529,404 | 7/1985 | Feinland et al. ........................ | 8/406 |
| 4,746,322 | 5/1988 | Herlihy .................................... | 8/405 |
| 4,776,857 | 10/1988 | Carroll et al. .......................... | 8/423 |
| 4,804,385 | 2/1989 | Grollier et al. ......................... | 8/423 |
| 4,808,190 | 2/1989 | Grollier et al. ......................... | 8/423 |
| 4,885,006 | 12/1989 | Grollier et al. ......................... | 8/423 |
| 4,888,027 | 12/1989 | Grollier et al. ......................... | 8/423 |
| 4,900,326 | 2/1990 | Grollier .................................... | 8/409 |

FOREIGN PATENT DOCUMENTS

| | | | |
|---|---|---|---|
| 0161073 | 11/1985 | European Pat. Off. | |
| 26841 | 9/1970 | Japan ..................................... | 548/469 |
| 45-26841 | 9/1970 | Japan ..................................... | 548/469 |

*Primary Examiner*—Linda Skaling Therkorn
*Attorney, Agent, or Firm*—Charles J. Zeller

[57] ABSTRACT

A process for preparing dye compositions which comprises hydrolyzing an O-protected 5,6-dihydroxyindole with an alkaline material under substantially anaerobic condition and the products made by such process.

6 Claims, No Drawings

DYE COMPOSITIONS CONTAINING 5,6-DIHYDROXY INDOLES AND A FOAM GENERATOR

This application is a continuation of application Ser. No. 138,992, filed Dec. 29, 1987, which is a continuation-in-part of application Ser. No. 761,950 filed Aug. 2, 1985, both now abandoned.

The invention relates to a process for preparing 5,6-dihydroxyindole dye compositions and to the products made by this process. More particularly it concerns a process and products of the aforementioned type that are useful in dyeing human hair and skin.

BACKGROUND OF THE INVENTION

The 5,6-dihydroxyindoles have been found to be very useful in dyeing hair, and particularly human hair on the head. Moreover, because of their inherent instability they have presented problems in their practical application. These instability problems are attested to in U.K. patent 797,174, U.S. Pat. No. 3,194,734 and U.S. Pat. No. 4,208,183 which are concerned with ways and means for preparing stable compositions containing these indole dyes.

U.K. patent 797,174 describes a process for preparing a dye composition containing 5,6-dihydroxyindoles and dyeing hair therewith. In accordance with this patent the 5,6-dihydroxyindoles are employed in the form of the 5,6diacetoxyindole compounds because of the stability of the latter. The diacetoxy compound is then deacetylated in aqueous solution with an alkalizing agent like monoethanolamine immediately prior to use, and the composition so formed is applied to hair. It is to be noted that this process is carried out in the presence of atmospheric oxygen.

U.S. Pat. No. 3,194,734 to Seemuller describes a process for dyeing hair with methyl substituted dihydroxyindoles which provide lighter color dyeouts than are provided by dihydroxyindole itself. The patent further teaches that alkaline solutions suitable for hair dyeing can be prepared immediately prior to dyeing by operating in a nitrogen atmosphere or by adding antioxidants such as thioglycollate, sulfite or the like. Based on the teachings of the prior art such solutions are not believed to have storage stability. The examples of the patent clearly show that, in presence of antioxidants, only weak colors such as light ash blond, gray, and bluish-gray are obtained by use of 5,6 dihydroxyindole unless extremely high levels of dye are employed. With the process of the present invention dark black dyeouts are produced, even after prolonged storage using very low levels of dye.

U.S. Pat. No. 4,208,183 teaches the preparation of storage stable solutions of dihydroxyindoles in alcoholic solvents. Prolonged storage of dihydroxyindoles is possible by this method, but these alcohol solutions are not suitable for dyeing hair, which is a serious disadvantage. Therefore, these storage stable solutions of the dihydroxyindoles must be mixed with a suitable cosmetic vehicle immediately prior to dyeing. The preferred method disclosed involves a dual compartment aerosol package. The reference does not disclose employing or storing the dihydroxyindoles under anaerobic conditions.

The present invention allows for storage in an aqueous medium which is suitable for dyeing hair directly rather than requiring a complex change of solvent and delivery system.

While 5,6-diacetoxyindole can be used as stable precursor for 5,6-dihydroxyindole, its use still presents difficulties since the 5,6-dihydroxyindole is sensitive to oxidation by atmospheric oxygen. This can lead to high loss of the dihydroxyindole due to its auto-oxidation outside the hair.

SUMMARY OF THE INVENTION

It has now been found that the above-mentioned difficulties can be avoided and stable compositions may be obtained if the alkaline hydrolysis of the O-protected 5,6-dihydroxyindole (I) is carried out under anaerobic conditions. As used herein the term O-protected refers to an acyloxy group or a sulfur containing group that is easily hydrolyzed to the free hydroxyl under alkaline conditions.

By the process of the present invention it is possible to produce storage stable, ready-to-use alkaline solutions of 5,6-dihydroxyindoles, which surprisingly do not form melanins until applied to the hair (or skin). Thus, much lower dye concentrations are needed to obtain dark dyeout. In the practice of this invention compound (I) will preferably be mixed with the hydrolyzing agent in a container which is substantially sealed to the atmosphere and the hydrolysis of compound (I) is permitted to slowly take place in this container. The present invention allows for storage in an aqueous medium which is suitable for dyeing hair directly rather than requiring a complex change of solvent and delivery systems.

DETAILED DESCRIPTION OF THE INVENTION

The O-protected hydroxyindoles that may be employed in the practice of the present invention correspond generally to the formula:

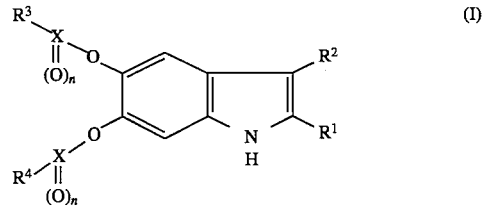

wherein $R^1$ and $R^2$ vary independently and may be hydrogen, methyl or ethyl. When $X=S$, $n=2$, $R^3$ and $R^4$ vary independently and maybe $C_1-C_6$ alkyl and substituted phenyl. When $X=C$, $n=1$, $R^3$ and $R^4$ vary independently and maybe $C_1-C_6$ alkyl, substituted phenyl and substituted benzyl. Typical of the alkyl groups which may be employed are methyl, ethyl, n-propyl, iso-propyl, n-butyl, isobutyl, t-butyl, n-pentyl, n-hexyl, etc. In the preferred forms of this invention lower alkyl radicals having from 1 to 4 carbon atoms and especially methyl are employed.

The indole employed will generally be 5,6-diacetoxyindole.

The quantity of O-protected 5,6-dihydroxyindole or 5,6-diacetoxyindole that will be employed in practicing the present invention may vary somewhat. Generally this will account for from about 0.25% to about 2% by weight based on the total weight of the composition with the preferred concentration being from about 1% to about 2% on the same weight basis.

The alkaline hydrolyzing agent that may be employed in carrying out the process of this invention may be any of a number of alkaline materials compatible with human use. These are exemplified by compounds such as monethanolamine, sodium hydroxide, potassium hydroxide, diethanolamine, ammonium hydroxide, triethanolamine, and morpholine. Very good results have been obtained with monoethanolamine which is the material of choice.

The quantity of alkaline hydrolyzing agent utilized in carrying out this invention may also vary and will be dependent on the quantity of O-protected 5,6-dihydroxyindole that is employed. Usually at least the theoretical quantity of alkaline agent is used which will completely hydrolyze off the protecting groups from the O-protected 5,6-dihyroxyindole compound i.e., at least 2 equivalents of alkaline agent. In the preferred practice from about 0.5% to about 10% by weight of alkaline agent is incorporated in a sealed container in accordance with the present invention.

Sufficient alkaline agent is added so that the pH of the composition is on the alkaline side and in the range from about pH 7 to about pH 11. The preferred pH will be from about pH 9 to about pH 9.5.

Other ingredients may also be included in the compositions of the invention. Thus an aqueous or dilute aqueous alcoholic vehicle containing up to 30% by weight of alcohol may be utilized as the medium in which the hydrolysis of the O-protected 5,6-dihydroxyindole takes place. Still other ingredients may also be employed which will be determined mainly by the form that the product will take. The aqueous or aqueous alcoholic vehicle when employed will comprise from about 0% to about 95% by weight based on the total weight of the composition.

In the practice of the present invention a variety of sealed containers may be utilized to provide the anaerobic conditions under which the O-protected 5,6-dihydroxyindole is hydrolyzed. Thus, for example, the components may be sealed in an aerosol can or included in a dispenser tube. In preparing the product in an aerosol can the O-protected 5,6-dihydroxyindole is dispersed or dissolved in an aqueous or aqueous alcoholic vehicle. To this is added enough alkalizing agent so that the final pH is about 9–9.5 which will be in excess of about 2 equivalents. This mixture is then rapidly sealed in an aerosol can with a propellant (e.g. hydrocarbon propellant) The hydrolysis of compound I is then allowed to slowly take place in the aerosol can under anaerobic conditions. This product then can be dispensed from the aerosol can when it is desired for use. The product has been tested for stability at 50° C. for 3 months and has been found to be satisfactory.

In addition to the ingredients mentioned above the aerosol products may also include other ingredients designed to improve the organoleptic qualities or facilitate the application of the product. Thus, it may include detergents, foam stabilizers, foaming agents, cationic polymers to diminish skin staining, etc. When the aerosol products are dispensed from the aerosol can they come out as rich foams that generally range in color from light yellow or tan to off-white or white.

In an alternative method for preparing the product of this invention, the ingredients may be packaged in a dispenser tube. The conditions within the tube are anaerobic in character and, as in the case with the aerosol products, compound I is permitted to slowly react with the alkaline agent to deprotect the O-protected 5,6-dihydroxyindole compound to produce the 5,6-dihydroxyindole.

The products made up in the dispenser tubes may be in the form of a gel or a shampoo. In preparing the product as a gel, compound (I) is dissolved in an aqueous vehicle (usually 95% ethanol). This is dissolved in a thickened aqueous solution (generally 3–6% Carbomer 940, with enough alkalyzing agent to remove the protecting groups (e.g. ca. 2 molar equivalents), and maintain the solution at pH 9.5 after hydrolysis is complete. The thickened solution is sealed in a tube, and hydrolysis is allowed to proceed slowly. The product is dispensed from the tube as necessary, and then the tube is resealed. The material remaining in the tube shows no loss in the ability to dye hair.

In preparing a product as a shampoo formulation, the compound I is dispensed in a shampoo base (e.g. Clairol Blue Shampoo), and alkalyzing agent sufficient to hydrolyze the protecting groups and adjust the pH to 9.5 (e.g. greater than 2 equivalents) is added. The composition is sealed in a suitable container and the compound I is allowed to slowly hydrolyze.

In addition to the ingredients mentioned above, the gel and shampoo formulations can also include other ingredients to improve the organoleptic qualities or facilitate application of the product. Thus, they may include, for example, cationic polymers to diminish skin staining, etc.

The hydrolysis of compound (I) in accordance with this invention is not instantaneous but proceeds over time. For optimum results, sufficient time should be allowed for complete conversion of compound(I) to the 5,6-dihydroxyindole as its mono or dianions. This will usually be about 18 hours at a pH of about 9.5.

In applying the products of this invention to the dyeing of hair it is often advantageous to employ them in conjunction with a promoter composition which accelerates the development of color from the 5,6-dihydroxyindole compound. Certain metal salt solutions, and especially solutions of $CuSO_4$ are particularly useful for this purpose. These solutions will generally be used at a cosmetically acceptable pH, the optimum being approximately pH 9.5. The concentration of the salts in this solution will generally be in the range of from about 0.25% to about 5% by weight based on the total weight of the solution with the preferred range being from about 1% to about 2% on the same weight basis.

In addition to the metal salt, and particularly $CuSO_4$, additional aids may be incorporated in the promoter composition. These may serve to facilitate the application of the promoter to the hair, to assist in the dyeing operation or to improve the elegance of the product or to improve the condition of the hair. Thus, for example, the distribution of the $CuSO_4$ in a liquid shampoo composition provides an effective means for getting it into the hair.

The application of the promoter composition will ordinarily take place as a separate step from the application of the 5,6-dihydroxyindole composition. The order in which these compositions are applied is not critical, that is to say that the promoter composition may first be applied to the hair followed by the application of the 5,6-dihydroxyindole composition or vice versa.

A convenient form for marketing the products of the present invention are as kits in which the promoter composition and the hair dye composition i.e., the 5,6-dihydroxyindole composition are each disposed in its own container and that both of these are packaged together for sale as a kit. With this arrangement the product is ready for use in the total hair treating and coloring operation.

The following examples are given to further illustrate the present invention. It is understood, however, that the invention is not limited thereto.

| Aerosol Product | | |
|---|---|---|
| | Gms. | % by Wt. |
| (1) 5,6-diacetoxyindole | 0.2 | 1.0 |
| (2) Monoethanolamine | 0.1 | 0.5 |
| (3) H$_2$O | 17.7 | 88.5 |
| *(4) Propellant 15A | 1.6 | 8.0 |
| (5) Cetyl alcohol | 0.4 | 2.0 |
| | 20.0 | 100.0 |

*75% difluoromethane/25% isobutane.

Procedure:

H$_2$O is added to solid 5,6 diacetoxyindole placed in an aerosol can. The cetyl alcohol and monoethanolamine then are added to the can which is rapidly capped and sealed. Air then is evacuated from the can through the aerosol valve and the propellant then is introduced into the can through the aerosol valve.

| Gel Product | | |
|---|---|---|
| | Gms. | % by Wt. |
| (1) 5,6-diacetoxyindole | 0.2 | 1.0 |
| (2) Monoethanolamine | 0.1 | 0.5 |
| (3) **Carbomer 940 (.5% solution in H$_2$O) | 19.7 | 98.5 |
| | 20.0 | 100.0 |

**CTFA nomenclature for cross-linked polymer of acrylic acid.

Procedure:

The Carbomer 940 solution is mixed with the 5,6-diacetoxyindole. The monoethanolamine is then added and the product is rapidly loaded into a dispenser tube and sealed.

An alternative, preferred procedure is to dissolve the the 5,6-diacetoxyindole (e.g. 1–5% by weight) in alcohol (e.g. 95% ethanol), and then add this solution to the thickened, alkalized Carbomer 940 solution under aerobic conditions. The product is then loaded into the dispenser tube and sealed.

EXAMPLE 3

| Shampoo | | |
|---|---|---|
| | Gms. | % by Wt. |
| (1) 5,6-diacetoxyindole | 0.2 | 1.0 |
| (2) Monoethanolamine | 0.1 | 0.5 |
| (3) Shampoo*** | 19.7 | 98.5 |
| | 20.0 | 100.0 |

***Shampoo Formula

| Ingredient | % by Wt. |
|---|---|
| Disodium monococamide MIPA-Sulfosoccinate | 10.000 |
| Methylparaben | .1000 |
| D&C Violet #2 | .0008 |
| FD&C Blue #1 | .0009 |
| Quaternium - 6 | 1.0000 |
| Imidazolidinyl urea | .2000 |
| Ethylenediamine tetra acetic acid | .0500 |
| Citric acid | .2000 |
| Sodium chloride | .6000 |
| Amphoteric - 12 | 4.5000 |
| Quaternium - 22 | 2.0000 |
| Ammonium lauryl sulfate | 40.0000 |
| Hydrolyzed animal protein | .4000 |
| Laureth - 23 | .0100 |
| Fragrance | .2000 |
| Water QS | 100. |

EXAMPLE 4

| Promoter Composition | | |
|---|---|---|
| | Gms. | % by Wt. |
| CuSO$_4$.5H$_2$O | 2.0 | 2 |
| Monoethanolamine | 5.0 | 5 |
| ****Conditioner Formula | 93.0 | 93 |
| | 100 | 100 |

****Conditioner Formula

| Ingredient | % by Wt. |
|---|---|
| Hydroxyethyl cellulose | 2.09250 |
| Sodium hydroxide | 0.01395 |
| Amphoteric - 2 | 2.38080 |
| Cocamidopropyl betaine | 1.86000 |
| Phosphoric acid | .42780 |
| Quaternium - 40 | 4.65000 |
| Ethoxydiglycol (and) Glycol (75-25) | 2.79000 |
| Sorbic acid, | 0.09300 |
| Quaternium - 15 | 0.09300 |
| Fragrance | 0.03720 |
| Water QS | 100 |

The conditioner solution composition is first formed by sequentially dissolving each of the ingredients in water (or, after addition of the first ingredient, the aqueous solution formed by addition of the previous ingredient).

The CuSO$_4$ is then dissolved in the conditioner solution and then the monoethanolamine is added resulting in a thin solution. This product is then poured into a bottle and the bottle is sealed.

It is believed that the reducing agents typically employed in prior art compositions adversely affect the dyeout, oxygen being a critical reactant in the formation of melanin from 5,6-dihydroxyindole and that the anhydrous organic solvents interfere with hair dyeing. The stabilized system of the present invention provides a dark black dyeout after storage. A series of comparisons using a $Cu^{+2}$ pretreatment clearly demonstrate these differences and the need for anaerobic conditions. These comparisons are set forth in Table I.

TABLE I

| | Hunter tristimulus values* | | |
|---|---|---|---|
| | L | a | b |
| Untreated blended gray hair | 32.24 | −0.64 | 6.26 |
| 1% 5,6-diacetoxyindole (anaerobic, pH 9) | 12.19 | −0.4 | −0.06 |
| 1% 5,6-diacetoxyindole (aerobic, pH 9) | 27.63 | −0.64 | 5.22 |
| 2% 5,6-diacetoxyindole (anaerobic, pH 9) | 9.93 | −0.09 | 0.12 |
| 1% 5,6-diacetoxyindole (in 100% ethanol) | 16.69 | −0.45 | 0.75 |

TABLE I-continued

|  | Hunter tristimulus values* | | |
|---|---|---|---|
|  | L | a | b |
| Nice 'n Easy 122 ® Natural black | 9.52 | −0.23 | 0.53 |

*Hunter values are a measure of reflected light and describe the color along three axes: L = 0 is black, L = 100 is white. The more positive "a" is, the redder the color, the more negative "a" is, the greener the color. Yellowness increases with increasing "b", value. Blueness increases with decreasing "b" value.

Kits may be prepared by packaging in the same outer package the aerosol, gel or shampoo products prepared by Examples 1, 2 or 3 above with the promoter product prepared in accordance with Example 4 above. In addition to the two products, if desired, there may also be included in the kit any auxiliary equipment or composition that would be useful in the application of the products to hair on the human head.

A feature of kits embodied in this invention may be the inclusion of a solution which may be used to modify or remove the color that may be generated on the head of a subject using the hair dye compositions contained in these kits. One such solution is a freshly prepared diluted aqueous alkaline $H_2O_2$ solution, which can affect these changes in a few minutes.

An illustrative, but not limiting example, of hair dyed by the kits described in Examples 1, 2 and 3 is the following. Hair is treated with an amount of promoter sufficient to wet the hair. This solution is left on the hair for ca. 5 minutes. The hair is rinsed thoroughly, and the dyeing solution (sufficient for coverage) is applied for 5 minutes. The hair is shampooed and dried, leaving a black color.

In a separate example, the order of application may be reversed.

In a further example, hair dyed by either of the previous method can be treated with dilute (1–6%) aqueous $H_2O_2$, adjusted to pH 9.5, to remove or modify the color as desired.

The foregoing embodiments and examples are set forth to illustrate the advantages to be achieved utilizing the present invention, reference being had to the appended claims for a definition of the scope of the invention.

We claim:

1. A dye composition for human keratinous fibers comprising 5,6-dihydroxyindole present in an amount effective to dye said human keratinous fibers and a foam generator, in an amount effective to generate foam, in a cosmetically acceptable aqueous medium, said composition being packaged, under pressure, in an aerosol device in the presence of a propellant agent, under such conditions so as to form a dyeing foam when dispensed from said aerosol device.

2. The dye composition of claim 1 wherein said commercially acceptable aqueous medium is an aqueous or aqueous alcoholic vehicle.

3. The dye composition of claim 1 wherein said propellant is a hydrocarbon propellant.

4. The dye composition of claim 1 wherein said aqueous medium has a pH ranging from 7 to 11.

5. The dye composition of claim 1 wherein said aqueous medium has a pH ranging from 9 to 9.5.

6. The dye composition of claim 1 or 5 wherein the foam generator is cetyl alcohol.

\* \* \* \* \*